US010417675B2

(12) United States Patent
Farraro et al.

(10) Patent No.: US 10,417,675 B2
(45) Date of Patent: Sep. 17, 2019

(54) SYSTEM AND METHOD FOR PROVIDING USER INTERFACES FOR FASHION SELECTION

(75) Inventors: Eric J. Farraro, San Jose, CA (US); John Tapley, Campbell, CA (US); Wei Diana Chiang, Saratoga, CA (US)

(73) Assignee: eBay Inc., San Jose, CA (US)

( * ) Notice: Subject to any disclaimer, the term of this patent is extended or adjusted under 35 U.S.C. 154(b) by 292 days.

(21) Appl. No.: 12/638,897

(22) Filed: Dec. 15, 2009

(65) Prior Publication Data
US 2010/0235259 A1    Sep. 16, 2010

Related U.S. Application Data

(63) Continuation of application No. 61/159,394, filed on Mar. 11, 2009.

(51) Int. Cl.
*G06Q 30/00* (2012.01)
*G06Q 30/06* (2012.01)

(52) U.S. Cl.
CPC ......... *G06Q 30/06* (2013.01); *G06Q 30/0601* (2013.01)

(58) Field of Classification Search
CPC .......................................... G06Q 30/06–30/08
USPC .................................. 705/26, 27, 26.1–27.2
See application file for complete search history.

(56) References Cited

U.S. PATENT DOCUMENTS 7,346,561 B1 *  3/2008  Devitt et al. .................... 705/27
8,006,197 B1 *  8/2011  Nevill-Manning .........................
                                                            G06F 17/30905
                                                            715/783
2002/0143565 A1 * 10/2002 Headings et al. ................. 705/1
2003/0028436 A1 *  2/2003 Razumov ......................... 705/26
2003/0065488 A1 *  4/2003 Beckert et al. .................... 703/1
2004/0039592 A1 *  2/2004 Shima ................................. 705/1
2005/0154487 A1 *  7/2005 Wang ............................ 700/132
2005/0234782 A1 * 10/2005 Schackne et al. .............. 705/27
2007/0271146 A1 * 11/2007 Nordmark et al. ............. 705/26
2008/0104039 A1 *  5/2008 Lowson ............................ 707/3
2008/0222262 A1 *  9/2008 Oh et al. ...................... 709/206
2008/0255920 A1 * 10/2008 Vandergriff et al. ........... 705/10
2009/0222127 A1 *  9/2009 Lind ............................. 700/132
2010/0191578 A1 *  7/2010 Tran et al. ...................... 705/10

(Continued)

OTHER PUBLICATIONS

"World Oil" (Euromoney Trading Limited, Jun. 2006).*

*Primary Examiner* — Ethan D Civan
(74) *Attorney, Agent, or Firm* — Schwegman Lundberg & Woessner, P.A.

(57) ABSTRACT

In various exemplary embodiments, a system and an associated method to retrieve information related to marketplace items within an electronic environment are disclosed. A network architecture comprises a listing module to store the information related to the marketplace items. The related information includes one or more user-created items such as an image of a model with one or more tagged items worn by the model. Each of the one or more tagged items has associated descriptive metadata. A communications module is arranged to receive a query including search terms related to social fashion items from an end-user. A query engine is coupled to the communications module to match the search terms contained within the query to the associated descriptive metadata of the tagged items in the listing module. A processing module then displays to the end-user the model and the one or more tagged items.

18 Claims, 9 Drawing Sheets

(56) References Cited

U.S. PATENT DOCUMENTS

2010/0191770 A1* 7/2010 Cho et al. .................... 707/783
2010/0211900 A1* 8/2010 Fujioka ........................ 715/765

* cited by examiner

US 10,417,675 B2

SYSTEM AND METHOD FOR PROVIDING USER INTERFACES FOR FASHION SELECTION

RELATED APPLICATION(S)

This application claims the benefit of priority under 35 U.S.C. 119(e) to Provisional Application No. 61/159,394, filed Mar. 11, 2009 and entitled "System and Method Allowing Social Fashion Selection in an Electronic Marketplace," which is incorporated herein by reference in its entirety.

TECHNICAL FIELD

The present application relates generally to the field of computer technology and, in a specific exemplary embodiment, to a system and method of allowing an end-user to select fashion and accessories in an electronic marketplace.

BACKGROUND

Design and selection of fashion articles of clothing and related accessories can be a time consuming and sometimes-daunting task. For example, clothing selection often involves traveling between various department stores and clothing shops, along with finding and trying on different articles of clothing at each location to determine aesthetic appearance. Accordingly, consumers are increasingly using on-line catalogs and other electronic marketing resources on the Internet for purchasing clothing and accessories. Although these on-line services offer convenience to consumers, they still are unable to provide guidance in terms of matching accessories to a given article of clothing or finding similar merchandise to match an outfit.

BRIEF DESCRIPTION OF DRAWINGS

Various ones of the appended drawings merely illustrate exemplary embodiments of the present invention and cannot be considered as limiting its scope.

DETAILED DESCRIPTION

Figure 1:
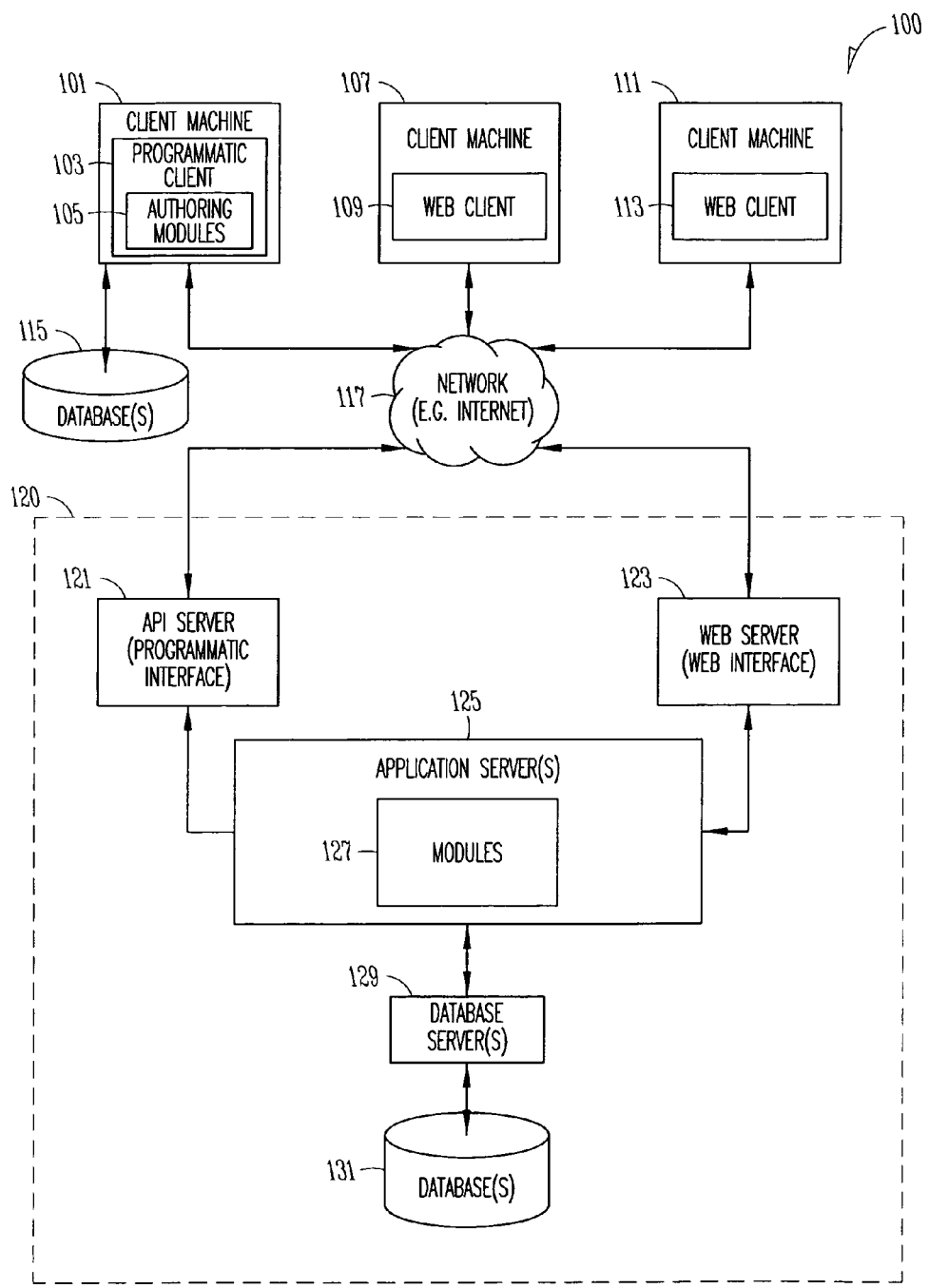
FIG. 1 is a block diagram illustrating an exemplary embodiment of a high-level client-server-based network architecture diagram depicting a system used to process end-user queries.

The description that follows includes illustrative systems, methods, techniques, instruction sequences, and computing machine program products that embody the present invention. In the following description, for purposes of explanation, numerous specific details are set forth to provide an understanding of various embodiments of the inventive subject matter. It will be evident, however, to those skilled in the art that embodiments of the inventive subject matter may be practiced without these specific details. Further, well-known instruction instances, protocols, structures, and techniques have not been shown in detail.

As used herein, the term "or" may be construed in either an inclusive or exclusive sense. Similarly, the term "exemplary" is construed merely to mean an example of something or an exemplar and not necessarily a preferred or ideal means of accomplishing a goal. Additionally, although various exemplary embodiments discussed below focus on social fashion in an electronic retail environment, the embodiments are given merely for clarity in disclosure. Thus, any type of electronic commerce or electronic business system and method, including various system architectures, may employ various embodiments of the social fashion system and method described herein and is considered as being within a scope of the present invention.

In an exemplary embodiment, a network architecture to retrieve information related to marketplace items within an electronic environment is disclosed. In various exemplary embodiments, the marketplace items relate to social fashion. The network architecture comprises a listing module to store the information related to the marketplace items. The related information includes one or more user-created items such as an image of a model with one or more tagged items worn by the model. Each of the one or more tagged items has associated descriptive metadata. A communications module is arranged to receive a query from an end-user, the query including search terms related to social fashion items. A query engine is coupled to the communications module to match the search terms contained within the query to the associated descriptive metadata of the tagged items in the listing module. A processing module then displays to the end-user the model and the one or more tagged items.

In another exemplary embodiment, a network architecture to create marketplace items in an electronic environment is disclosed. The network architecture includes an image selection page to select an image of a model such as, for example, a celebrity. A listing module stores one or more user-created items including the model with one or more tagged items selected by a seller. Each of the one or more tagged items has associated descriptive metadata. A communications module is arranged to receive a query from an end-user, the query including search terms related to social fashion items. A query engine is coupled to the communications module to match the search terms contained within the query to the associated descriptive metadata of the tagged items in the listing module. A processing module then displays to the end-user the model and the one or more tagged items.

In another exemplary embodiment, a system for retrieving information related to marketplace items within an electronic environment is disclosed. The system includes a listing means for storing the information related to the marketplace items. The information includes user-created items that have an image of a model, such as, for example, a celebrity. The model has one or more tagged items with each of the tagged items having associated descriptive metadata. A communications module receives a query from an end-user and a query means matches constraints contained within the query to the associated descriptive metadata of the tagged items in the listing means. A processing module displays to the end-user the model and the one or more tagged items.

In another exemplary embodiment, a method to retrieve information related to marketplace items within an electronic environment is disclosed. The method includes storing the information related to the marketplace items. The information includes user-created items that have an image of a model with one or more tagged items. Each of the one or more tagged items has associated descriptive metadata. A query is received from an end-user and an additional query is performed to match constraints contained within the query to the associated descriptive metadata of the tagged items. The one or more tagged items are then displayed to the end-user.

In another exemplary embodiment, a computer-readable storage medium is disclosed. The computer-readable storage medium stores instructions that, when executed by a processor, cause the processor to perform a method to retrieve information related to marketplace items within an electronic environment. The method includes storing the information related to the marketplace items. The information includes user-created items that have an image of a model with one or more tagged items. Each of the one or more tagged items has associated descriptive metadata. A query is received from an end-user and an additional query or search is performed to match constraints contained within the query to the associated descriptive metadata of the tagged items. The one or more tagged items are then displayed to the end-user. Each of these exemplary embodiments, and others, is discussed in detail, below.

With reference to FIG. 1, a high-level network diagram of an exemplary embodiment of a system 100 with a client-server architecture includes a first client machine 101, a second client machine 107, a third client machine 111, a network 117 (e.g., the Internet), and an information storage and retrieval platform 120. In this embodiment, the information storage and retrieval platform 120 constitutes a commerce platform or commerce server and provides server-side functionality, via the network 117, to the first 101, second 107, and third 111 client machines. A programmatic client 103 in the form of authoring modules 105 executes on the first client machine 101. A first web client 109 (e.g., a browser, such as the Internet Explorer browser developed by Microsoft Corporation of Redmond, Wash.) executes on the second client machine 107. A second web client 113 executes on the third client machine 111. Additionally, the first client machine 101 is coupled to one or more databases 115.

Turning to the information storage and retrieval platform 120, an application program interface (API) server 121 and a web server 123 are coupled to, and provide programmatic and web interfaces respectively to, one or more application servers 125. The application servers 125 host one or more modules 127 (e.g., modules, applications, engines, etc.). The application servers 125 are, in turn, coupled to one or more database servers 129 facilitating access to one or more information storage databases 131. The one or more modules 127 provide a number of information storage and retrieval functions and services to users accessing the information storage and retrieval platform 120. The one or more modules 127 are discussed in more detail, below.

While the exemplary system 100 of FIG. 1 employs a client-server architecture, a skilled artisan will recognize that the present disclosure is not limited to such an architecture. The exemplary system 100 could equally well find application in, for example, a distributed, or peer-to-peer, architecture system. The one or more modules 127 and the authoring modules 105 may also be implemented as stand-alone software programs, which do not necessarily have networking capabilities.

The first 109 and second 113 web clients access the one or more modules 127 via the web interface supported by the web server 123. Similarly, the programmatic client 103 accesses the various services and functions provided by the one or more modules 127 via the programmatic interface provided by the API server 121. The programmatic client 103 is, for example, a seller application (e.g., the "Turbo Lister 2" application developed by eBay Inc., of San Jose, Calif.) enabling sellers to author and manage data items or listings on the information storage and retrieval platform 120 in an off-line manner. Further, batch-mode communications can be performed between the programmatic client 103 and the information storage and retrieval platform 120. In addition, the programmatic client 103 can include, as previously indicated, the authoring modules 105 used to author, generate, analyze, and publish domain rules and aspect rules. The domain and aspect rules are used in the information storage and retrieval platform 120 to structure the data items and transform queries. Such domain and aspect rules are known independently in the art.

Figure 2:
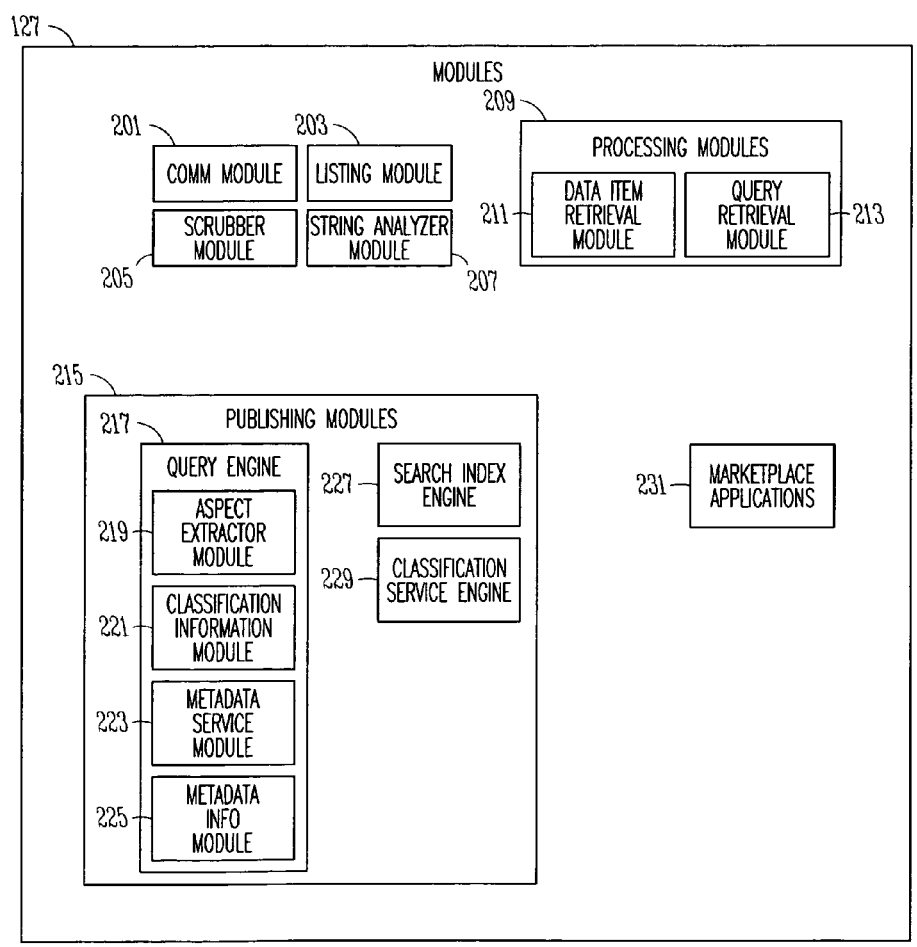
FIG. 2 is a block diagram illustrating an exemplary embodiment of various modules of the network architecture of FIG. 1.

Referring now to FIG. 2, an exemplary block diagram of the one or more modules 127 of FIG. 1 includes a communication module 201, a listing module 203, a scrubber module 205, a string analyzer module 207, a plurality of processing modules 209, and a publishing module 215. The one or modules 127 further includes a marketplace application block 231.

The communication module 201 receives a query from one or more of the client machines 101, 107, 111 (see FIG. 1). The query includes one or more constraints (e.g., keywords, categories, or information specific to a type of data item). The communication module 201 interacts with a query engine 217 and a search index engine 227, both located in the publishing module 215, to process the query. In conjunction with the query engine 217 and the search index engine 227, the communication module 201 attempts to extract aspect-value pairs (e.g., brand="Donna Karan") based on the query. Details of the aspect-value pairs are described in more detail, below.

The publishing module 215 publishes new or existing rules, as discussed above with reference to FIG. 1, to the information storage and retrieval platform 120, thereby enabling the rules to be operative (e.g., applying the rules to data items and queries). In a specific exemplary embodiment, the information storage and retrieval platform 120 of FIG. 1 may be embodied as a network-based marketplace that supports transactions of data items or listings (e.g., goods or services) between sellers and buyers. One such marketplace is eBay, The World's Online Marketplace®, developed by eBay Inc., of San Jose, Calif. In this embodiment, the information storage and retrieval platform 120 receives information from sellers describing the data items. The data items are subsequently retrieved by potential buyers or bidders. The one or more modules 127 include the marketplace application block 231 to provide a number of marketplace functions and services to end-users accessing the information storage and retrieval platform 120.

The publishing module 215 further includes a classification service engine 229. The classification service engine 229 applies domain rules to identify one or more domain-value pairs (e.g., product type=women's blouses) associated with the data item. The classification service engine 229 further applies the aspect rules to identify aspect-value pairs associated with the data item. The classification service engine 229 applies the domain and aspect rules to data items or listings as they are added to the information storage and retrieval platform 120 or responsive to the publication of new rules (e.g., domain rules or aspect rules). The scrubber module 205 utilizes services of the classification service engine 229 to structure the item information in the data item (e.g., the classification service engine 229 applies domain and aspect rules). The classification service engine 229 then pushes or publishes item search information over a bus (not shown but implicitly understood by a skilled artisan) in real time to the search index engine 227.

The search index engine 227 includes search indexes and data item search information (e.g., including data items and associated domain-value pairs and aspect-value pairs). The search index engine 227 receives the transformed query from the communication module 201 and utilizes the search indexes to identify data items based on the transformed query. The search index engine 227 communicates the found data items to the communication module 201.

A query retrieval module 213, within the plurality of processing modules 209, receives information from one or more of the client machines 101, 107, 111 and stores the information as a data item in the one or more information storage databases 131 (see FIG. 1). For example, an end-user, acting as a seller and operating on one of the client machines, enters descriptive information for the data item to be offered for sale or auction through the information storage and retrieval platform 120.

The plurality of processing modules 209 receives classification information and metadata information associated with the data item. The information is published to, for example, a local backend server (not shown) hosting the query engine 217, the search index engine 227, and the classification service engine 229.

The plurality of processing modules 209 further includes a data item retrieval module 211 to receive requests for data items from a client machine. For example, responsive to receiving a request, the data item retrieval module 211 reads data items from the data item information stored on the one or more information storage databases 131 (FIG. 1) and stores the data items as sample information in the one or more databases 115 for access by the client machine. Responsive to receiving the request, the query retrieval module 213 reads queries from the sample information and communicates the queries to the client machine.

The string analyzer module 207 receives requests from the first client machine 101 to identify candidate values to associate with an aspect. The request may include the aspect and one or more values that have been associated with the aspect. The string analyzer module 207 utilizes the aspect (e.g., "color") to identify strings of text in a database that includes the aspect. The string analyzer module 207 relies on various services provided in the information storage and retrieval platform 120 to identify and process the strings of text. For example, the string analyzer module 207 utilizes services that expand the aspect to a derivative form of the aspect including a singular form (e.g., "color"), a plural form (e.g., "colors"), a synonymous form, an alternate word form (e.g., "chroma," "coloring," or "tint"), a commonly misspelled form (e.g., "collor"), or an acronym form.

A database (not shown specifically) used by the string analyzer module 207 includes queries or data items that have been entered by a user (e.g., buyer or seller, respectively although a seller may wish to enter queries as well) to the information storage and retrieval platform 120. The database can also store or reference dictionaries, thesauruses, or other reference sources. The string analyzer module 207 analyzes the strings of text to identify candidate values to associate with the aspect. More examples of query strings and searching techniques are given, below.

The query engine 217 includes an aspect extractor module 219, a classification information module 221, a metadata service module 223, and a metadata information module 225. The aspect extractor module 219 receives a query from the communication module 201 and applies aspect rules to extract aspect-value pairs from the query. Further, the aspect extractor module 219 communicates the query received from the communication module 201 to the plurality of processing modules 209 that stores the query as sample query information.

The classification information module 221 includes phrases from a plurality of past searches to reference against the query. For example, synonyms or related information for a query can be stored in the classification information module 221 to aid a user in locating an item or a particular set of items.

The metadata service module 223 communicates descriptive metadata information to the communication module 201 based on a query received from the communication module 201. The metadata information is retrieved from the metadata information module 225 and includes metadata that the communication module 201 uses to format and generate a user interface to provide additional information to the user based on the original user-generated query.

Once aspect-value pairs, classification information, and other relevant information is retrieved through, for example, either the data item retrieval module 211 or the query retrieval module 213, the listing module 203 provides additional assistance to a user listing the data item. The additional assistance can be, for example, one or more interfaces for the user to upload photographs, textual descriptions, and bidding information.

Although the one or more modules have been defined in terms of a variety of individual modules and engines, a skilled artisan will recognize that many of the items can be combined or organized in other ways. The description given herein simply provides an exemplary embodiment to aid the reader in an understanding of the systems and methods used herein.

Application of Social Fashion Selection into the Exemplary Network Architecture

Figure 3:
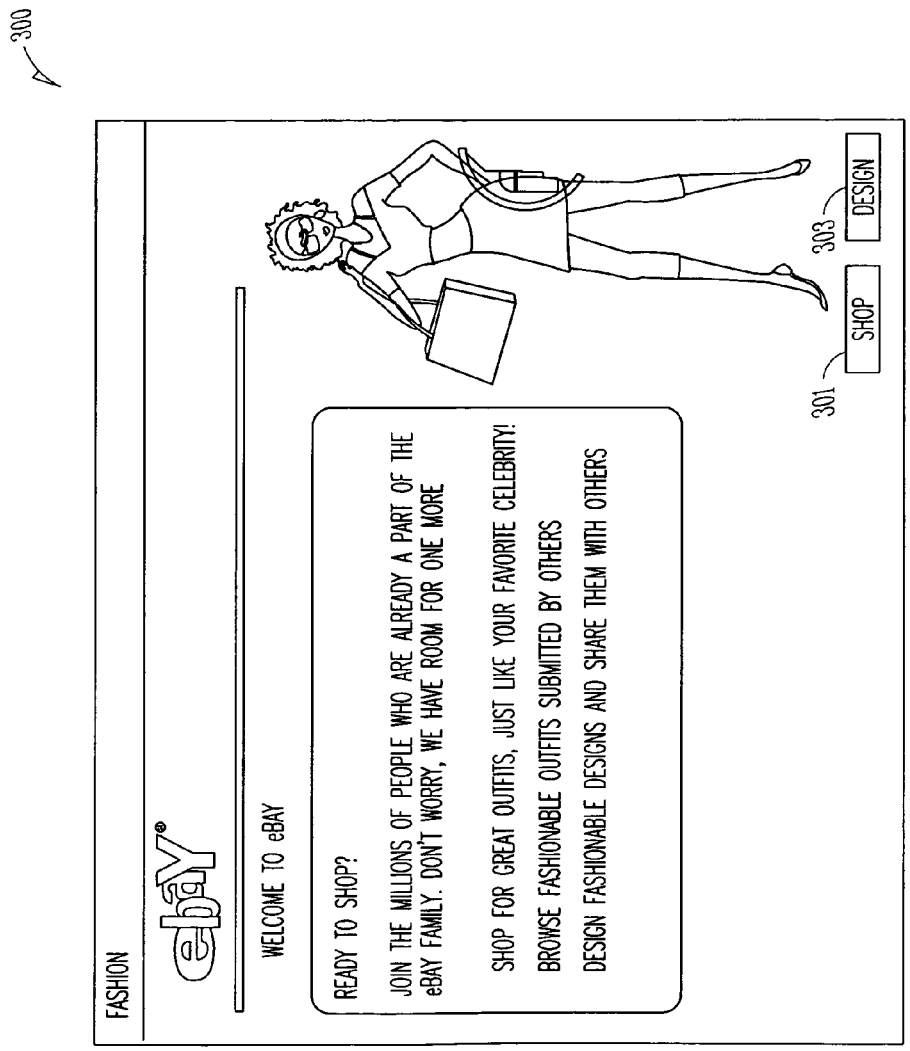
FIG. 3. is an exemplary screen shot of a social fashion electronic marketplace entry portal.

Referring now to FIG. 3, a screen shot of an entry portal 300 allows a user to access a plurality of social fashion web pages. The user selects either a shop button 301 or a design button 303 for entry into one set of the plurality of social fashion web pages. By selecting the shop button 301, the user enters a webpage directed to browsing existing designs (e.g., designs directed to fashion items created by other users such as a widget view page discussed with reference to FIG. 6, below).

Alternatively, by selecting the design button 303, the user can create new designs. Any new designs created by the user can be shared with other end-users.

Figure 4:
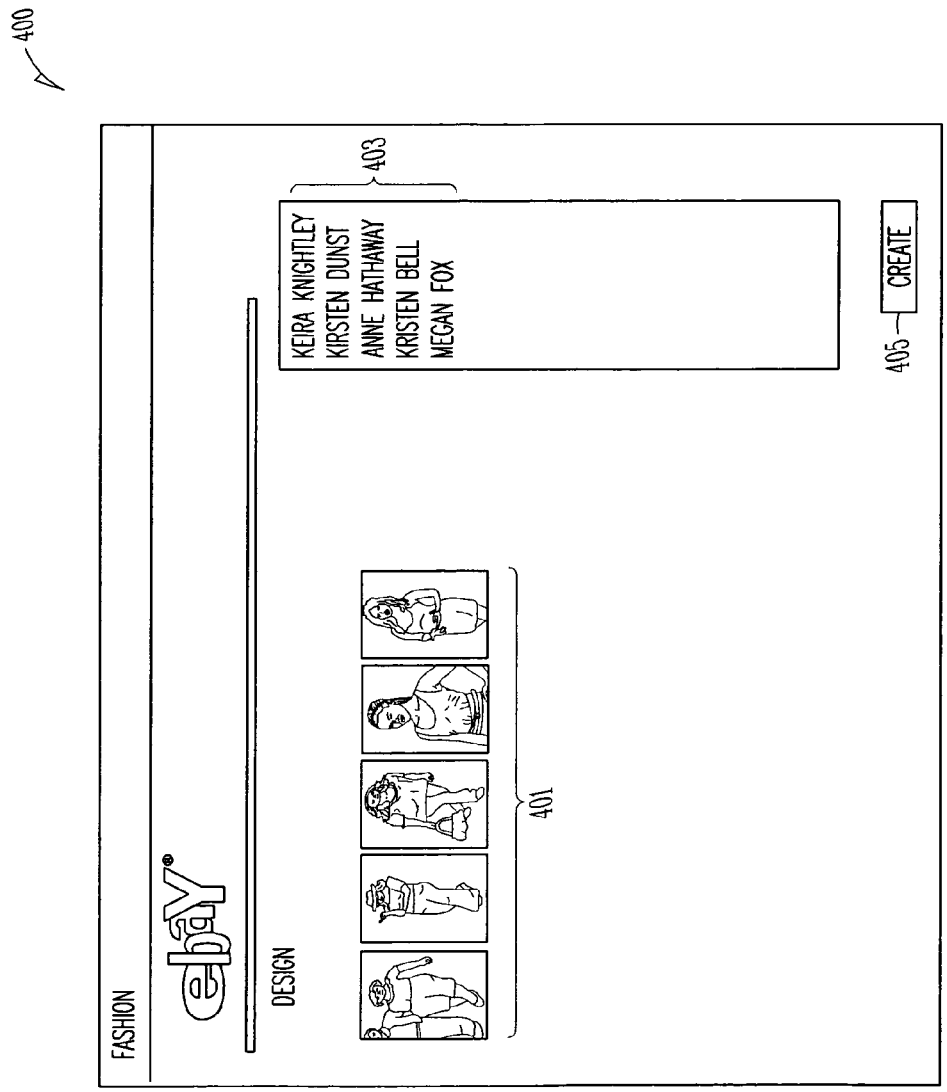
FIG. 4 is another exemplary screen shot of any celebrity image helper page in the electronic marketplace of FIG. 3.

Once the user has selected the design button 303, a celebrity image helper page 400 of FIG. 4 appears. The celebrity image helper page 400 includes a plurality of celebrity images 401 and an associated list 403 of celebrity names. The user selects a celebrity from either the plurality of celebrity images 401 or the associated list 403 of celebrity names. As described in more detail below, a celebrity is chosen as a realistic online model for tagging fashion items (e.g., such as clothing, shoes, and other accessories). Alternatively, the user can upload his or her own photograph (not shown) to be used as the realistic online model. In yet another embodiment (not shown but independently understood by a skilled artisan), the user can select an avatar to be used as the online model. Once the online model is selected, the user selects a create button 405.

Figure 5:
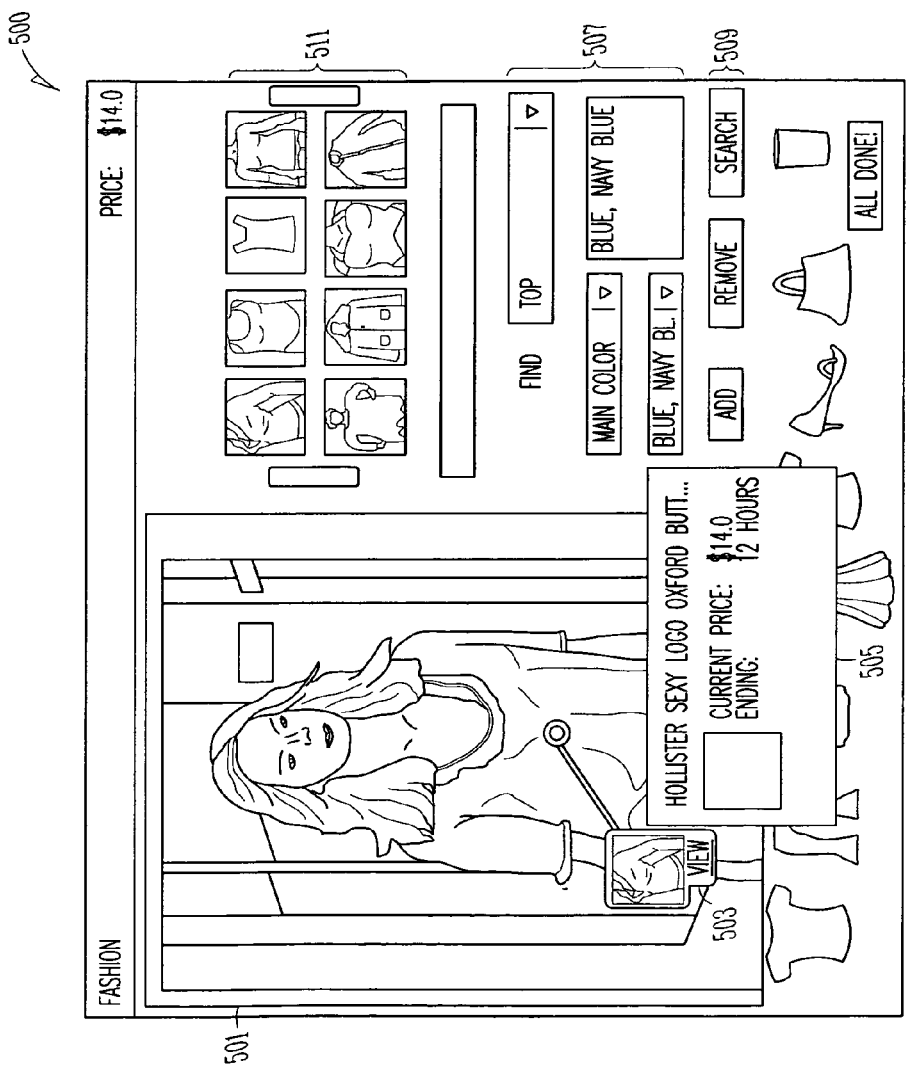
FIG. 5 is a screen shot of the celebrity image of FIG. 4 showing tagged clothing items in a main editor view.

With reference now to FIG. 5, a main editor view 500 for creating new designs or viewing existing designs includes an image or photograph 501 of the online model selected from the celebrity image helper page 400. In an exemplary embodiment, the user creates a plurality of tagged items 503 that another user (e.g., a buyer or bidder) can later view for either bidding on or purchasing. For each of the plurality of tagged items 503 that the user creates, a brief description and current price (either for bidding or purchasing) are entered and created in an information window 505. Although not shown, a user could also tag a variety of other items worn or carried by the online model. For example, if the online model was carrying a purse, the purse could also be tagged by the user and similar items resembling the purse can be added.

In this embodiment, the user has tagged a particular type of "top" or blouse available for bid or purchase in the electronic marketplace. Attributes (e.g., aspect-value pairs) of the blouse have been previously entered into the various modules and engines as described above with reference to FIG. 2. Attributes used to search for similar items can be entered by the buyer. Alternatively or in addition, either yet another user or a maintainer of the celebrity image helper page 400 of FIG. 4 can enter or add to the attributes associated with the celebrity image.

Alternatively, once the user has tagged items on the online model, the user selects a category of the item from, for example, a drop-down box (not shown). Similar drop-down boxes can provide sub-categories such as size, color, and other attributes. The drop-down series of boxes thus assist the user in creating the user-created listing.

The main editor view 500 further includes a find item block 507 and a selection block 509. The user can enter new or additional attributes in the find item block 507. For example, the user can add additional clothing, shoes, or accessories (CSA) to match the blouse. The buyer can then select a main color of the CSA item to either match or complement the blouse. The buyer can additionally select additional attributes such as secondary or tertiary colors. The search button within the selection block 509 is selected and the electronic marketplace is searched for items meeting the criteria provided. The search query process is described with reference to FIG. 2, above. An image result block 511, based on the buyer's search criteria, displays retrieved items in a grid-like format. The buyer then selects individual items from the image result block 511 and iteratively adds or removes items by additional searches and selecting the add or remove buttons from the selection block 509. Once the main editor view is completed, the user-created outfit with tagged items for bid or sale is save on, for example, the one or more information storage databases 131 of FIG. 1. The user-created outfit is displayed through the listing module 203 of FIG. 2.

In a specific exemplary embodiment, the main editor view 500 is implements in Flex, an Adobe® Flash® product. However, many other software packages are known independently in the art to implement the main editor.

Figure 6:
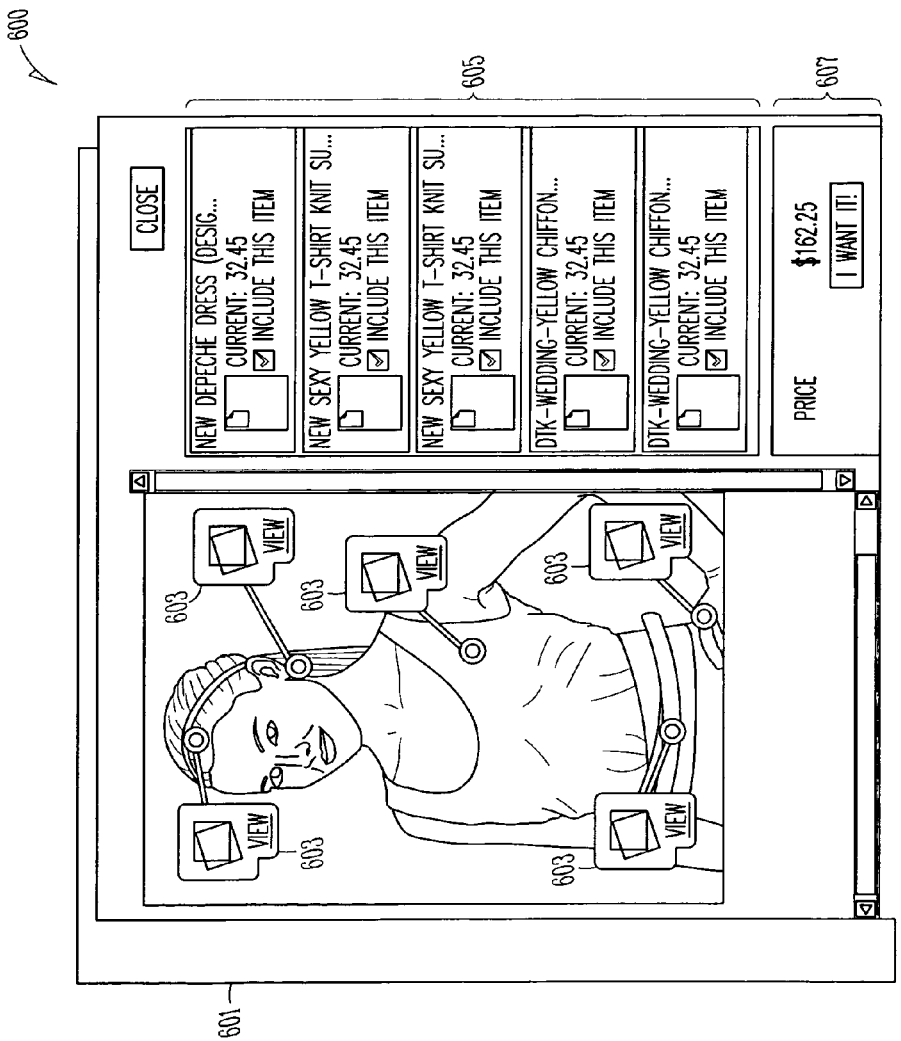
FIG. 6 is an exemplary screen shot of a user-created widget view.

With reference to FIG. 6, in an alternative embodiment to the main editor view 500 of FIG. 5, a widget view 600 is created by another user (i.e., a seller). The widget view 600 includes an image or photograph 601 of a celebrity and includes a plurality of tagged items 603: a headband, earrings, a dress, a belt, and a ring. Each of the plurality of tagged items 603 includes a textual description and current price or bid within a side bar 605.

Each of the plurality of tagged items 603 may be originally entered into the electronic marketplace by the seller as described with reference to FIGS. 1 and 2, above. The user (e.g., the buyer) can select any of the plurality of tagged items 603 by selecting each desired item through the textual description of the side bar 605. Alternatively, the user is presented with a total price block 607 and can purchase all items shown by selecting the "I want it!" button within the total price block 607.

In a specific exemplary embodiment (not shown), sellers could also embed the widget view 600 in separate electronic marketplace listings, web pages, or external web sites. Further, the widget view 600 can also include a social features block (not shown) to solicit commenting and voting of the items within the widget view 600 by the electronic community.

Figure 7:
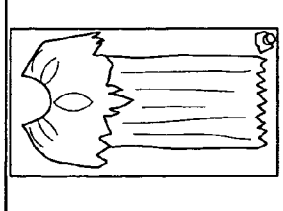
FIG. 7 is an exemplary screen shot of a view item page including a "find matching outfits" button.

Referring now to FIG. 7, a view item page 700 includes an image or photograph and textual description block 701 as well as a "Find Matching Outfits" button 703. When the user selects the "Find Matching Outfits" button 703, the electronic marketplace automatically performs a query for other items having similar attributes to the one identified in the photograph and textual description block 701. The automatic query is performed using previously entered and underlying descriptive metadata, attribute, and aspect-value information associated with the item(s) in the photograph and textual description block 701 as noted above with reference to FIG. 2. Further, selecting the "Find Matching Outfits" button 703 can display the widget view 600 as described with reference to FIG. 6, above. Alternatively, selecting the "Find Matching Outfits" button 703 can produce a grid-like display (not shown) of matching outfits or CSA.

Figure 8:
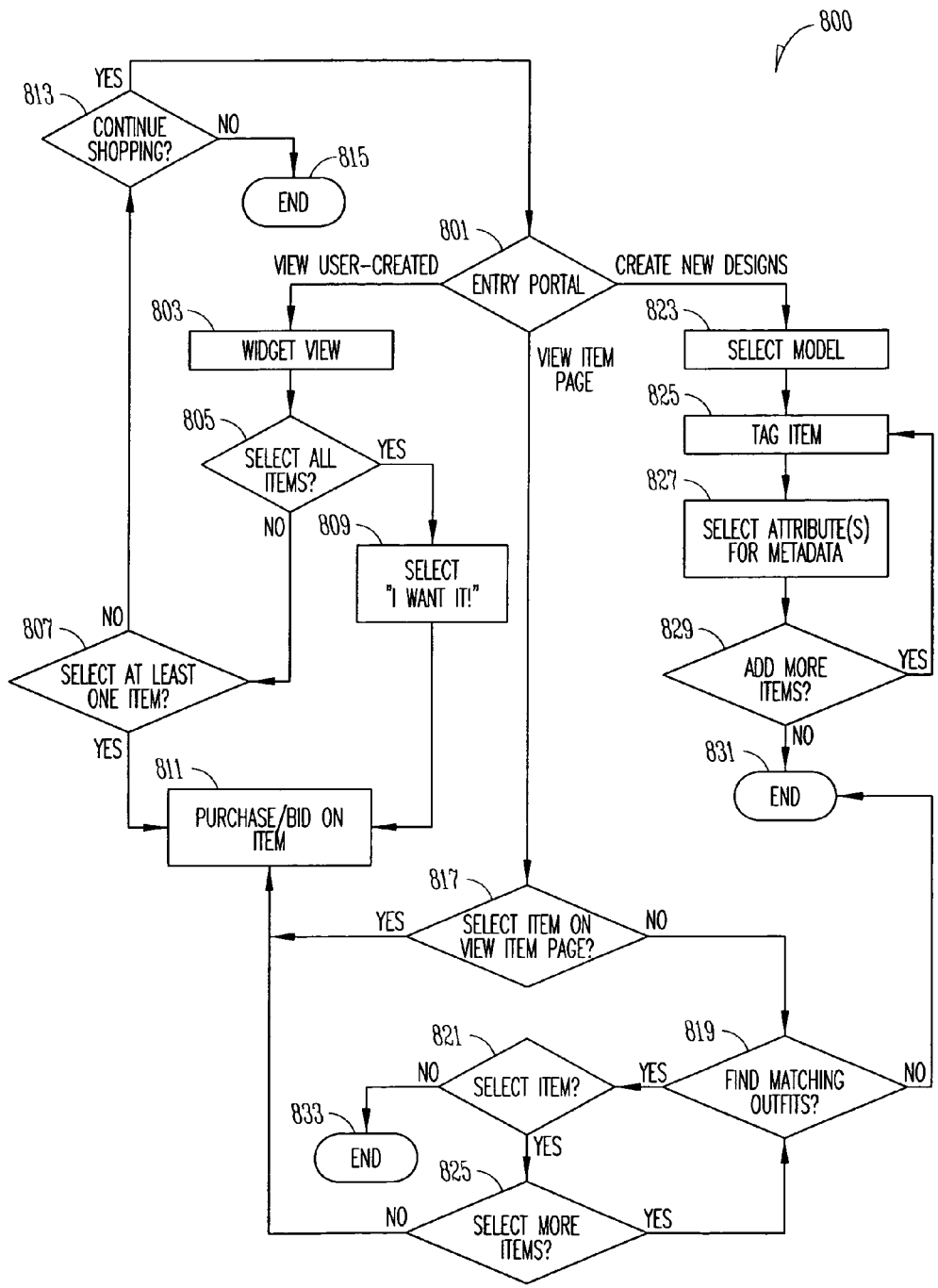
FIG. 8 is an exemplary method of use of the social fashion electronic marketplace.

With reference to FIG. 8, an exemplary method 800 of social fashion selection includes an entry portal 801 in which the user chooses to view user-created designs, view an item page, or create new designs. Continuing reference will be made to select ones of FIGS. 4-7 concurrently with the discussion of the exemplary method 800 of FIG. 8.

The user selecting to view user-created designs is taken to the widget view page 803. The widget view page 803 is described in more detail with reference to FIG. 6, above. After the user arrives at the widget view page 803, a determination is made 805 whether the user chooses to select all items shown on that page. The user choosing to select all items selects, at operation 809, the "I Want It!" button. At operation 811, the user then purchases or bids on the item or items (or, alternatively, may add the item to a watch list). If, at operation 805, the user chooses not to select all items, a determination is made 807 whether the user chooses to select at least one item. If the user selects at least one item, the user then purchases or bids on the item or items at operation 811. However, if at operation 807, the user chooses to not select at least one item, a determination is made 813 whether the user chooses to continue shopping. If not, the process flow ends 815. If the user chooses to continue shopping, the user is brought back to the entry portal 801.

With continuing reference to FIG. 8 and concurrent reference now to FIG. 7, if at the entry portal 801, the user chooses to view the item page, a determination is made 817 whether the user chooses to select an item shown on the view item page. If the user chooses to select the item, the user then purchases or bids on the item at operation 811.

Alternatively, if the user chooses not to select the item on the view item page, a determination is made 819 whether the user chooses to find outfits matching the one displayed on the view item page. If the user chooses to find more matching outfits, a determination is made 821 whether the user chooses to select the item. If an item is not selected, the process flow ends 833. However, if the user selects the item at operation 821, an additional determination is made 825 whether the user chooses to select more items. If the user does not select more items, the user may purchase or bid on the item at operation 811. If the user does choose to select more items at operation 825, the user again finds matching outfits at operation 819 or simply ends 831 the process.

With continuing reference to FIG. 8 and concurrent reference now to FIGS. 4 and 5, if at the entry portal 801 the user chooses to create new designs, the user selects a model at operation 823. The user then tags an item 825 and selects one or more attributes associated with the tagged item that is stored as metadata at operation 827. A determination is made 829 whether the user chooses to tag or add more items. If the user does not choose to tag more items, a user created page consisting of the chosen model from operation 823 along with the metadata and other associated attributes are saved in, for example, the one or more information storage databases 131 of FIG. 1. The user-created page is displayed by accessing the page from the listing module 203 of FIG. 2. Alternatively, if the user chooses to add more items at operation 829, the user may then tag additional items to add to the user's listing.

A skilled artisan will recognize that the exemplary method of social fashion selection described above can take on a variety of alterations and permutations. The exemplary method 800 is simply provided as illustrative of ways in which the disclosed inventive subject matter may be implemented.

Moreover, a skilled artisan will also recognize that selecting a vehicle of social fashion merely highlights the inventive nature of particular embodiments of the present invention. For example, the embodiments described herein can also relate to various types of items for sale or bid in an electronic marketplace. Rather than selecting a human model, as described with reference to FIGS. 4 and 8, a user can either choose or upload any type of photograph, model, avatar, or drawing to implement the method disclosed. In a specific exemplary embodiment, a picture of a specific room in the user's home can be uploaded. Items in the room are then tagged and described with various attributes and aspect-value pairs as described above or, alternatively or in addition, associated with similar items already listed within the electronic marketplace. The tagged room items are then prepared as a new user listing.

Therefore, while various embodiments of the present invention are described with reference to assorted implementations and exploitations, it will be understood that these embodiments are illustrative only and that a scope of the present inventions is not limited merely to those described embodiments. Moreover, the social fashion selection systems and methods described herein may be implemented with facilities consistent with any hardware system or hardware systems either defined herein or known independently in the art using techniques described herein. Many variations, modifications, additions, and improvements are therefore possible.

Modules, Components, and Logic

Additionally, certain embodiments described herein may be implemented as logic or a number of modules, components, or mechanisms. A module, logic, component, or mechanism (collectively referred to as a "module") may be a tangible unit capable of performing certain operations and is configured or arranged in a certain manner. In certain exemplary embodiments, one or more computer systems (e.g., a standalone, client, or server computer system) or one or more components of a computer system (e.g., a processor or one or more processors) may be configured by software (e.g., an application or application portion) or firmware (note that software and firmware can generally be used interchangeably herein as is known by a skilled artisan) as a module that operates to perform certain operations described herein.

In various embodiments, a module may be implemented mechanically or electronically. For example, a module may comprise dedicated circuitry or logic that is permanently configured (e.g., within a special-purpose processor) to perform certain operations. A module may also comprise programmable logic or circuitry (e.g., as encompassed within a general-purpose processor or other programmable processor) that is temporarily configured by software or firmware to perform certain operations. It will be appreciated that a decision to implement a module mechanically, in the dedicated and permanently configured circuitry, or in temporarily configured circuitry (e.g., configured by software) may be driven by cost and time considerations.

Accordingly, the term module should be understood to encompass a tangible entity, be that an entity that is physically constructed, permanently configured (e.g., hardwired), or temporarily configured (e.g., programmed) to operate in a certain manner and/or to perform certain operations described herein. Considering embodiments in which modules or components are temporarily configured (e.g., programmed), each of the modules or components need not be configured or instantiated at any one instance in time. For example, where the modules or components comprise a general-purpose processor configured using software, the general-purpose processor may be configured as respective different modules at different times. Software may accordingly configure the processor to constitute a particular module at one instance of time and to constitute a different module at a different instance of time.

Modules can provide information to, and receive information from, other modules. Accordingly, the described modules may be regarded as being communicatively coupled. Where multiples of such modules exist contemporaneously, communications may be achieved through signal transmission (e.g., over appropriate circuits and buses) that connect the modules. In embodiments in which multiple modules are configured or instantiated at different times, communications between such modules may be achieved, for example, through the storage and retrieval of information in memory structures to which the multiple modules have access. For example, one module may perform an operation, and store the output of that operation in a memory device to which it is communicatively coupled. A further module may then, at a later time, access the memory device to retrieve and process the stored output. Modules may also initiate communications with input or output devices and can operate on a resource (e.g., a collection of information).

Exemplary Machine Architecture and Machine-Readable Storage Medium

Figure 9:
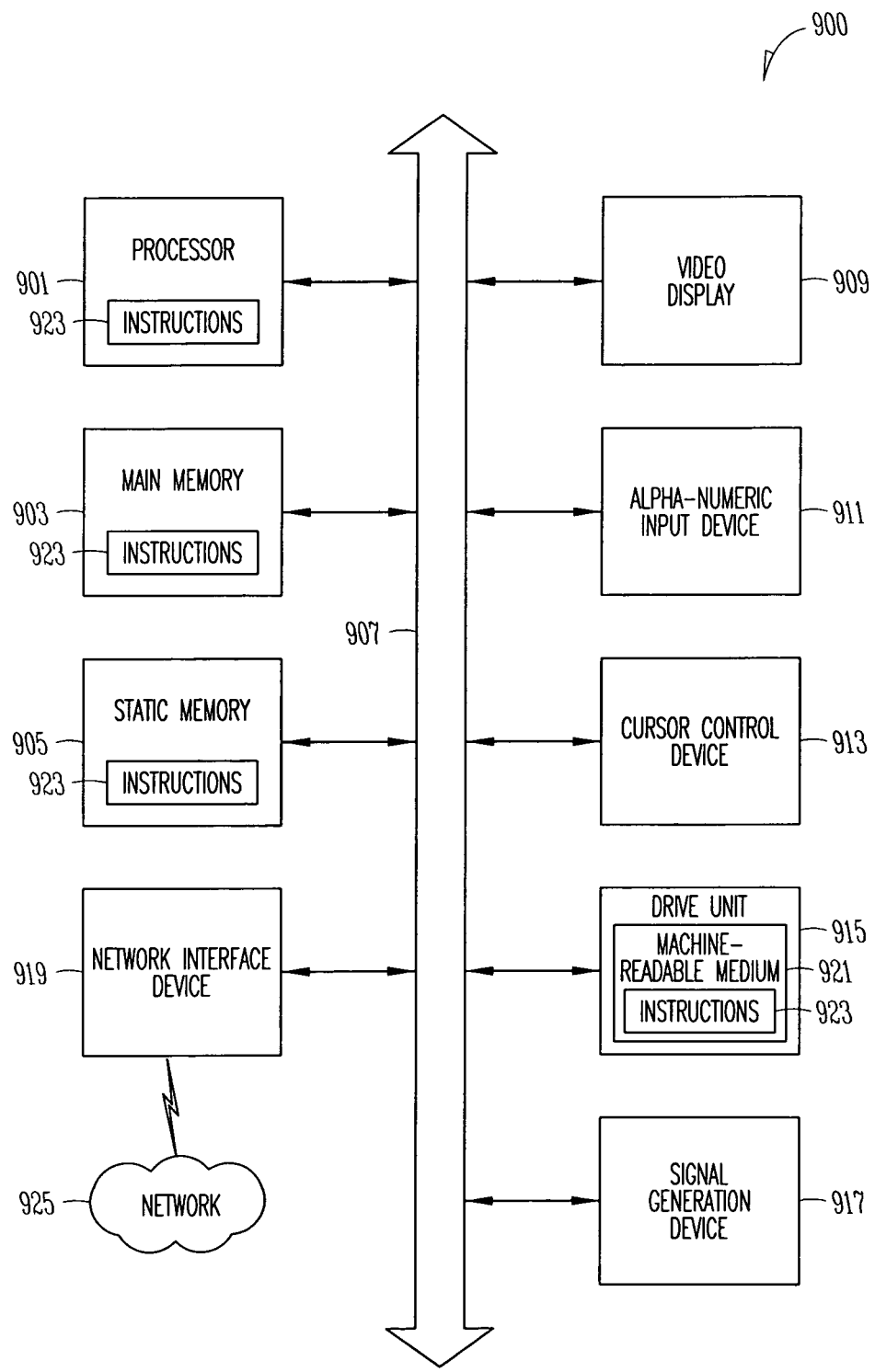
FIG. 9 is a simplified block diagram of a machine in an exemplary form of a computing system within which a set of instructions, for causing the machine to perform any one or more of the methodologies discussed herein, may be executed.

With reference to FIG. 9, an exemplary embodiment extends to a machine in the exemplary form of a computer system 900 within which instructions, for causing the machine to perform any one or more of the methodologies discussed herein, may be executed. In alternative exemplary embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, a switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The exemplary computer system 900 includes a processor 901 (e.g., a central processing unit (CPU), a graphics processing unit (GPU) or both), a main memory 903 and a static memory 905, which communicate with each other via a bus 907. The computer system 900 may further include a video display unit 909 (e.g., a liquid crystal display (LCD) or a cathode ray tube (CRT)). The computer system 900 also includes an alphanumeric input device 911 (e.g., a keyboard), a user interface (UI) navigation device 913 (e.g., a mouse), a disk drive unit 915, a signal generation device 917 (e.g., a speaker), and a network interface device 919.

Machine-Readable Medium

The disk drive unit 915 includes a machine-readable medium 921 on which is stored one or more sets of instructions and data structures (e.g., software 923) embodying or used by any one or more of the methodologies or functions described herein. The software 923 may also reside, completely or at least partially, within the main memory 903 or within the processor 901 during execution thereof by the computer system 900; the main memory 903 and the processor 901 also constituting machine-readable media.

While the machine-readable medium 921 is shown in an exemplary embodiment to be a single medium, the term "machine-readable medium" may include a single medium or multiple media (e.g., a centralized or distributed database, or associated caches and servers) that store the one or more instructions. The term "machine-readable medium" shall also be taken to include any tangible medium that is capable of storing, encoding, or carrying instructions for execution by the machine and that cause the machine to perform any one or more of the methodologies of the present invention, or that is capable of storing, encoding, or carrying data structures used by or associated with such instructions. The term "machine-readable medium" shall accordingly be taken to include, but not be limited to, solid-state memories, and optical and magnetic media. Specific examples of machine-readable media include non-volatile memory, including by way of exemplary semiconductor memory devices (e.g., EPROM, EEPROM, and flash memory devices); magnetic disks such as internal hard disks and removable disks; magneto-optical disks; and CD-ROM and DVD-ROM disks.

Transmission Medium

The software 923 may further be transmitted or received over a communications network 925 using a transmission medium via the network interface device 919 utilizing any one of a number of well-known transfer protocols (e.g., HTTP). Examples of communication networks include a local area network (LAN), a wide area network (WAN), the Internet, mobile telephone networks, Plain Old Telephone (POTS) networks, and wireless data networks (e.g., WiFi and WiMax networks). The term "transmission medium" shall be taken to include any intangible medium that is capable of storing, encoding, or carrying instructions for execution by the machine, and includes digital or analog communications signals or other intangible medium to facilitate communication of such software.

Although an overview of the inventive subject matter has been described with reference to specific exemplary embodiments, various modifications and changes may be made to these embodiments without departing from the broader spirit and scope of the present invention. Such embodiments of the inventive subject matter may be referred to herein, individually or collectively, by the term "invention" merely for convenience and without intending to voluntarily limit the scope of this application to any single invention or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present invention. In general, structures and functionality presented as separate resources in the exemplary configurations may be implemented as a combined structure or resource. Similarly, structures and functionality presented as a single resource may be implemented as separate resources.

These and other variations, modifications, additions, and improvements fall within a scope of the present invention is represented by the appended claims. The specification and drawings are, accordingly, to be regarded in an illustrative rather than a restrictive sense.

What is claimed is:

1. A system comprising:
   one or more hardware processors; and
   memory storing instructions that, when executed by the one or more hardware processors, cause the one or more hardware processors to perform operations comprising:
   causing presentation of a first user interface on a device of a user, the first user interface displaying an image of an article of clothing;
   receiving, at the system via the first user interface, a first selection of the image of the article of clothing displayed on the first user interface, the first selection triggering a search to find one or more clothing items that match an attribute associated with the image of the article of clothing;
   in response to receiving the first selection, accessing, by the system, stored information from one or more databases, the stored information including a plurality of data items that each includes an image of a model with a clothing item and associated metadata, the model in one or more of the plurality of data items being a celebrity model;

based on the attribute associated with the image of the article of clothing, performing the search for the one or more matching clothing items from the accessed stored information, the search comprising comparing the attribute associated with the image of the article of clothing to the associated metadata; and in response to the search, causing display of a second user interface, the second user interface including an image for each of the one or more matching clothing items and a corresponding price.

2. The system of claim 1, wherein the operations further comprise receiving a selection of a matching clothing item from the one or more matching clothing items, the selection allowing the user to purchase the matching clothing item.

3. The system of claim 1, wherein the second user interface comprises a grid-like display of the one or more matching clothing items.

4. The system of claim 1, wherein the attribute used to perform the search comprises a color associated with the article of clothing.

5. The system of claim 1, wherein the operations further comprise receiving an upload of the image of the article of clothing.

6. The system of claim 1, wherein each of the plurality of data items are tagged with the associated metadata by a seller of a corresponding clothing item.

7. A method comprising:
causing, by a networked system, presentation of a first user interface on a device of a user, the first user interface displaying an image of an article of clothing;

receiving, at the networked system via the first user interface, a first selection of the image of the article of clothing displayed on the first user interface, the first selection triggering a search to find one or more clothing items that match an attribute associated with the image of the article of clothing;

in response to receiving the first selection, accessing, by a hardware processor of the networked system, stored information from one or more databases, the stored information including a plurality of data items that each includes an image of a model with a clothing item and associated metadata, the model in one or more of the plurality of data items being a celebrity model;

based on the attribute associated with the image of the article of clothing, performing the search for the one or more matching clothing items from the accessed stored information, the search comprising comparing the attribute associated with the image of the article of clothing to the associated metadata; and in response to the search, causing display of a second user interface, the second user interface including an image for each of the one or more matching clothing items and a corresponding price.

8. The method of claim 6, further comprising receiving a selection of a matching clothing item from the one or more matching clothing items, the selection allowing the user to purchase the matching clothing item.

9. The method of claim 6, wherein the second user interface comprises a grid-like display of the one or more matching clothing items.

10. The method of claim 6, wherein the attribute used to perform the search comprises a color associated with the article of clothing.

11. The method of claim 6, further comprising receiving an upload of the image of the article of clothing.

12. The method of claim 6, wherein each of the plurality of data items are tagged with the associated metadata by a seller of a corresponding clothing item.

13. A non-transitory machine readable medium having instructions that, when executed by one or more hardware processors of a machine, cause the machine to perform operations comprising:
causing presentation of a first user interface on a device of a user, the first user interface displaying an image of an article of clothing;

receiving, via the first user interface, a first selection of the image of the article of clothing displayed on the first user interface, the first selection triggering a search to find one or more clothing items that match an attribute associated with the image of the article of clothing;

in response to receiving the first selection, accessing stored information from one or more databases, the stored information including a plurality of data items that each includes an image of a model with a clothing item and associated metadata, the model in one or more of the plurality of data items being a celebrity model;

based on the attribute associated with the image of the article of clothing, performing the search for the one or more matching clothing items from the accessed stored information, the search comprising comparing the attribute associated with the image of the article of clothing to the associated metadata; and in response to the search, causing display of a second user interface, the second user interface including an image for each of the one or more matching clothing items and a corresponding price.

14. The non-transitory machine readable medium of claim 12, wherein the operations further comprise receiving a selection of a matching clothing item from the one or more matching clothing items, the selection allowing the user to purchase the matching clothing item.

15. The non-transitory machine readable medium of claim 12, wherein the second user interface comprises a grid-like display of the one or more matching clothing items.

16. The non-transitory machine readable medium of claim 12, wherein the attribute used to perform the search comprises a color associated with the article of clothing.

17. The non-transitory machine readable medium of claim 12, wherein the operations further comprise receiving an upload of the image of the article of clothing.

18. The non-transitory machine readable medium of claim 12, wherein each of the plurality of data items are tagged with the associated metadata by a seller of a corresponding clothing item.

* * * * *

UNITED STATES PATENT AND TRADEMARK OFFICE
CERTIFICATE OF CORRECTION

PATENT NO. : 10,417,675 B2  
APPLICATION NO. : 12/638897  
DATED : September 17, 2019  
INVENTOR(S) : Eric J. Farraro et al.

Page 1 of 1

It is certified that error appears in the above-identified patent and that said Letters Patent is hereby corrected as shown below:

On the Title Page

In item (60), in Column 1, in "Related U.S. Patent Documents", Line 1, delete "Continuation of" and insert -- Provisional --, therefor.

In the Claims

In Column 13, Line 55, in Claim 8, delete "claim 6," and insert -- claim 7, --, therefor.

In Column 14, Line 1, in Claim 9, delete "claim 6," and insert -- claim 7, --, therefor.

In Column 14, Line 4, in Claim 10, delete "claim 6," and insert -- claim 7, --, therefor.

In Column 14, Line 7, in Claim 11, delete "claim 6," and insert -- claim 7, --, therefor.

In Column 14, Line 9, in Claim 12, delete "claim 6," and insert -- claim 7, --, therefor.

In Column 14, Lines 39-40, in Claim 14, delete "claim 12," and insert -- claim 13, --, therefor.

In Column 14, Lines 44-45, in Claim 15, delete "claim 12," and insert -- claim 13, --, therefor.

In Column 14, Lines 47-48, in Claim 16, delete "claim 12," and insert -- claim 13, --, therefor.

In Column 14, Lines 50-51, in Claim 17, delete "claim 12," and insert -- claim 13, --, therefor.

In Column 14, Lines 53-54, in Claim 18, delete "claim 12," and insert -- claim 13, --, therefor.

Signed and Sealed this  
Twenty-eighth Day of July, 2020

Andrei Iancu  
*Director of the United States Patent and Trademark Office*